(12) United States Patent
Healey

(10) Patent No.: US 7,716,997 B2
(45) Date of Patent: May 18, 2010

(54) PARASITIC TAGS FOR ACTION ANNOTATION

(75) Inventor: Jennifer Healey, Waltham, MA (US)

(73) Assignee: Intel Corporation, Santa Clara, CA (US)

( * ) Notice: Subject to any disclaimer, the term of this patent is extended or adjusted under 35 U.S.C. 154(b) by 34 days.

(21) Appl. No.: 11/854,529

(22) Filed: Sep. 12, 2007

(65) Prior Publication Data

US 2009/0069637 A1    Mar. 12, 2009

(51) Int. Cl.
    *G01L 1/00* (2006.01)
(52) U.S. Cl. ................................. 73/862.381
(58) Field of Classification Search ............ 73/862.381; 600/300, 587; 340/573.1; 602/16
    See application file for complete search history.

(56) References Cited

U.S. PATENT DOCUMENTS

| 4,383,252 | A | * | 5/1983 | Purcell et al. ............... 340/606 |
| 5,269,081 | A | * | 12/1993 | Gray ........................... 36/136 |
| 5,558,638 | A | | 9/1996 | Evers |
| 6,112,224 | A | | 8/2000 | Peifer |
| 6,302,844 | B1 | | 10/2001 | Walker |
| 6,315,740 | B1 | * | 11/2001 | Singh .......................... 600/595 |
| 6,450,953 | B1 | * | 9/2002 | Place et al. .................. 600/300 |
| 6,544,171 | B2 | | 4/2003 | Beetz |
| 7,106,222 | B2 | * | 9/2006 | Ward et al. ..................... 341/34 |
| 7,181,192 | B2 | * | 2/2007 | Panasik et al. ........... 455/404.1 |
| 7,294,105 | B1 | * | 11/2007 | Islam ......................... 600/300 |
| 7,319,400 | B2 | * | 1/2008 | Smith et al. .............. 340/573.1 |
| 2005/0107726 | A1 | * | 5/2005 | Oyen et al. .................... 602/16 |

OTHER PUBLICATIONS

International Search Report and Written Opinion for International Application No. PCT/US2008/074605, mailed Feb. 25, 2009, 11 Pages.

* cited by examiner

*Primary Examiner*—Jewel Thompson
(74) *Attorney, Agent, or Firm*—Caroline M. Fleming

(57) ABSTRACT

A sensing device is used to consolidate and time-synchronize Intensive Care Unit (ICU) or other clinical data from patient monitoring devices provided by a plurality of different vendors having proprietary event data formats. The automation of logging of events due to external forces applied to patient monitoring devices detected by the sensing device improves the timing in and completeness of nurses' notes. Furthermore, the sensing device provides an easy way to synchronize or consolidate data from multiple vendors' patient monitoring devices.

20 Claims, 4 Drawing Sheets

PARASITIC TAGS FOR ACTION ANNOTATION

FIELD

This disclosure relates to medical devices and in particular to collecting event data from patient monitoring devices.

BACKGROUND

Medical facilities such as hospitals use monitoring and medical equipment from multiple vendors using different vendor proprietary formats. Thus, it is extremely difficult to consolidate the data collected.

In current practice, caregivers (medical professionals) such as nurses visit patients' rooms to adjust medications and attend to alarms generated by the patient monitoring equipment. Many visits merely involve turning off an alarm on the patient monitoring device after verifying the health of the patient. The caregiver later notes the visit, the tasks performed and the records the time of the visit. However, often these recorded times are not accurate, as these handwritten notes are typically typed into a computerized entry system many hours later, likely at the end of the caregiver's shift.

BRIEF DESCRIPTION OF THE DRAWINGS

Features of embodiments of the claimed subject matter will become apparent as the following detailed description proceeds, and upon reference to the drawings, in which like numerals depict like parts, and in which:

Figure 1:
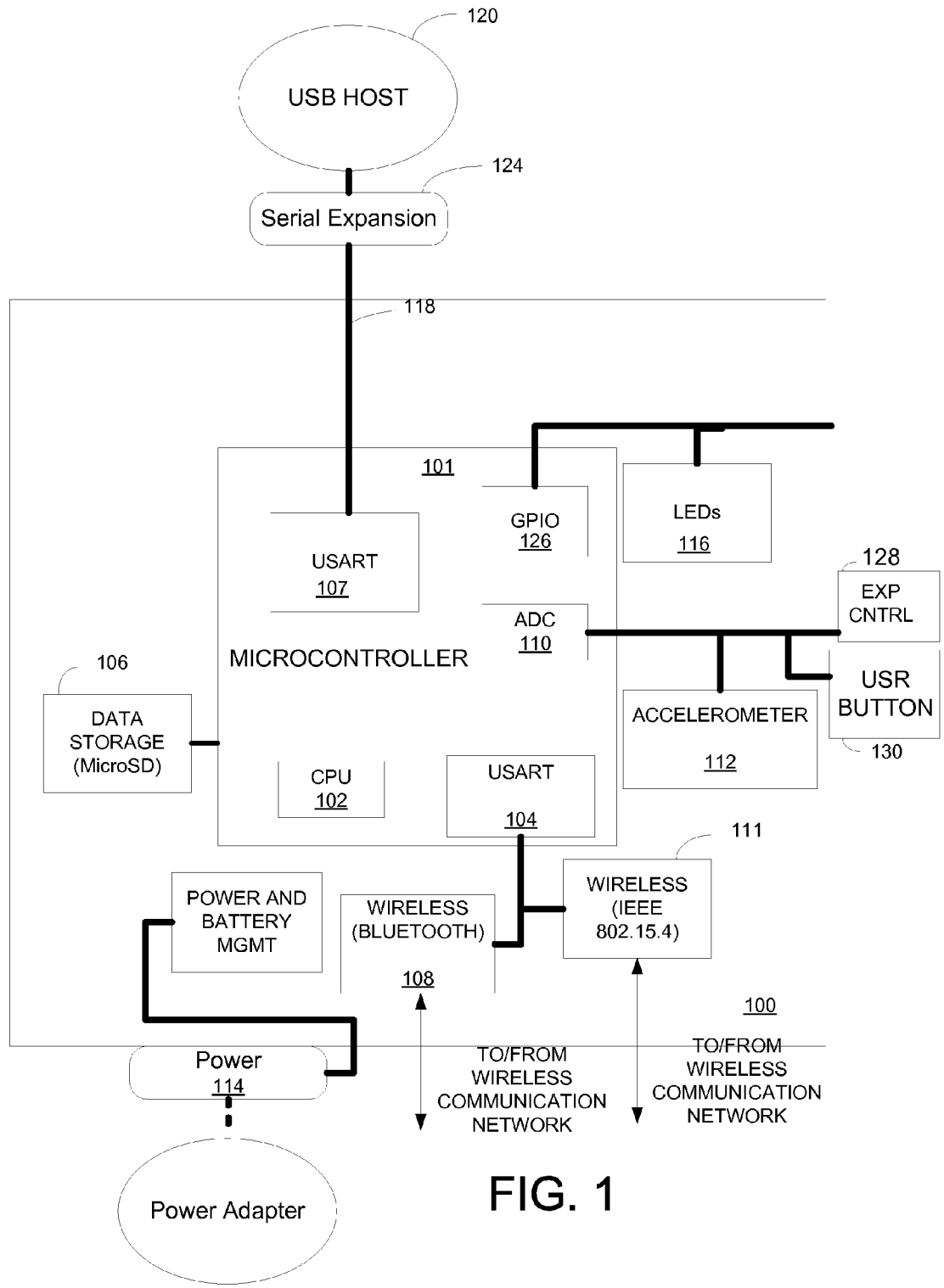
FIG. 1 is an embodiment of a sensing device to collect events from a patient monitoring device according to the principles of the present invention.

Although the following Detailed Description will proceed with reference being made to illustrative embodiments of the claimed subject matter, many alternatives, modifications, and variations thereof will be apparent to those skilled in the art. Accordingly, it is intended that the claimed subject matter be viewed broadly, and be defined only as set forth in the accompanying claims.

DETAILED DESCRIPTION

Medical professionals have expressed an interest in collecting automatic event annotation to augment and improve a caregiver's notes and to better interpret Intensive Care Unit (ICU) records. However, it is difficult to access information on events collected by patient monitoring devices due to the plurality of vendor proprietary formats used to transmit event data from these monitoring devices.

In addition to difficulty in supporting multiple vendor proprietary formats, patient monitoring devices for sale in the United States are subject to approval by the Food and Drug Administration (FDA).

In an embodiment of the present invention, a sensing device that is not electrically coupled to the patient monitoring device is placed on the patient monitoring device to automatically collect event data that would otherwise be inaccessible due to vendor proprietary formats.

When the caregiver is compiling notes to be placed in the patient's medical records, the event data collected from the sensing device may suggest corrected times or highlight actions that a caregiver, for example, a medical professional such as a nurse, doctor or medical practitioner may have forgotten to record or recorded an estimated time. For example a caregiver may record that new intravenous line (IV) was started at 4:00 a.m. but the sensing device may have sensed a change at 3:39 a.m., the caregiver may accept or reject the recorded event in his/her final report. For example, a sensing device that detects motion of an electrocardiogram (ECG) monitoring device may note that the sensing device detected motion at a certain time and prompt the caregiver to confirm or deny that a change in electrocardiogram (ECG) monitoring occurred.

Patient monitoring devices may include means for recording and storing events typically using a proprietary format. Patient monitoring equipment such as a medical device monitored by a caregiver includes ECG monitoring devices that may include means for recording and storing events and an intravenous line (IV) stand or IV pole that provides support for hanging an IV bag that is coupled to an IV line. The IV line is a soft, flexible catheter that is inserted into a vein to deliver a fluid stored in the IV bag. The IV line may also be coupled to a fluid monitor than controls the rate of flow of the fluid from the IV bag. Patient monitoring devices such as an IV stand that do not include means for recording events may include audible alarms that indicate that there may be problem with the flow of fluid from the IV bag through the IV line to the patient. The audible alarm may be activated perhaps due to a blockage in the IV line or due to the IV line being physically removed from the patient's vein.

In an embodiment of the present invention, a sensing device includes a housing that includes a sensor that detects an event due to an external force applied to a patient monitoring device when the housing is in physical contact with the patient monitoring device. The sensing device has no electrical connection to the patient monitoring device and no communications path to the patient monitoring device. The sensing device may include a wireless network communication interface to transmit stored time-stamped events to a remote system over the wireless network.

Accelerometer based action detection may be used to determine motion of a non-intelligent device, for example, a sensing device may be attached to a drawer in a kitchen cabinet to detect movement of the drawer, for example, movement due to opening or closing the drawer. An indication of the detected movement may be transmitted to a remote processing device and recorded in the remote processing device. However, accelerometer based action detection may not independently infer indirect actions. For example, the mere indication that the drawer moved may not be used to infer that an object was removed from the drawer. This may even have been a false reading of the accelerometer due to echo readings.

However, the action annotation when used in conjunction with some other measure such as a nurse's notes, physiological data or other information can be used to corroborate the time of an event. For example, a nurse may write "Morphine administered at 1:30 PM" in his/her notes. Later, the record is reviewed against the accelerometer record. The accelerometer record may indicate that movements of the IV stand were actually recorded at 1:17 PM but no movements were recorded at 1:30. From the accelerometer record, it may be reasonable to conclude that the actual dosage was administered at 1:17 instead of 1:30. The inaccuracy in the time may be that the time on the room clock or the nurse's watch was incorrect or that the nurse estimated the time because he/she did not get a chance to write down the information until later in his/her shift.

In current practice it is probably not considered that important exactly when the dose is given, but in medical research it is very important, especially when researching physiological reactions to drugs. As medicine and medical treatments become more sophisticated and tailored, precision in drug delivery timing will become more and more important. A more important consideration in clinical practice is providing additional evidence about actions that may have happened and not been recorded, for example if a patient was supposed to have had a drug change at a particular time and the IV bag looks as if it had been changed, yet there was no direct written record of the action, the IV accelerometer record could provide additional evidence as to whether or not the something had been done with the IV and give a likely indication of when that action had occurred.

FIG. 1 is an embodiment of a sensing device 100 to collect events from a patient monitoring device according to the principles of the present invention. The sensing device 100 includes one or more action sensors for detecting events. In an embodiment, an action sensor may be an accelerometer sensor, switch or set of switches. The action sensor may be connected through the serial expansion port 124 or through the expansion port 128. In the embodiment shown in FIG. 1, a user button 130 is shown coupled to the sensing device 100.

The sensing device 100 includes a microcontroller 101 that controls the operation of the sensing device 100 and communicates to various peripherals through internal and external expansion modules. In the embodiment shown in FIG. 1, the microcontroller 101 includes a General Purpose Input/Output Interface (GPIO) 126, an Analog-to-Digital converter (ADC) interface 110, two Universal Asynchronous/Synchronous Receive/Transmit serial communication (USART)s 104, 107, memory (not shown), and a multi-port memory controller 102. The ADC interface 110 is used to capture sensor data from one or more Analog-to-Digital converter (ADC) channels. In an embodiment, there may be up to 8 ADC channels. In an embodiment, the microcontroller 101 may include memory components such as Random Access Memory (RAM), or Flash memory (non-volatile memory). The Flash memory may store both data and instructions (code). The code stored in the Flash memory may include functions for collecting events detected by the sensing device and transmitting these events to a collection device over a communications network. The microcontroller 101 may also include a Central Processing Unit (CPU) 102 that may be a 16-Bit Reduced Instruction Set Computer (RISC) CPU. In order to maintain low-power usage the ADC interface 110 may be disabled when not in use and re-enabled when necessary. The USARTs 104, 107 enable serial peripheral interface (SPI) and asynchronous USART functionality. In an embodiment, one of the USARTs 104, 107 allows Inter-Integrated Circuit (I2C) communication and has two specific Direct Memory Access (DMA) channels to ensure maximum throughput with data rates up to 400 Kbps. In an embodiment, the Institute of Electrical and Electronics Engineers (IEEE) 802.15.4 wireless network communications interface 111 is connected to the USART 104 using SPI mode.

In an embodiment the ADC interface 110 may support up to 8 ADC channels for 12-bit Analog/Digital (A/D) conversions using a 16 word conversion-and-control buffer which enables data to be read and stored without the need for CPU intervention. External ADC ports may be utilised for reading data from an accelerometer 112

The accelerometer 112 may be coupled to the ADC interface 110 to enable reading of 3-dimensional acceleration. In an embodiment the accelerometer 112 may be a Freescale Semiconductor™ 3-axis (XYZ) accelerometer (MMA7260Q). The accelerometer 112 may be connected to the MSP430 via three channels of the ADC. An internal expansion through the ADC interface 110 allows modules that support other sensing functions to be coupled to the sensing device 100. A signal captured by a sensor device coupled to the sensing device 100 received at an ADC port may be forwarded by the microcontroller 101 to a processing (collection) device over a wireless communication network through the Bluetooth® module 108. The standard wireless communication protocols (Bluetooth® and IEEE 802.15.4) supported by the sensing device 100 may provide a range of 50 m or more from an access port or a collection device over the wireless communication network. An optional memory device, for example, data storage 106 may be coupled to the multi-port memory controller 102 in the microcontroller 101. In one embodiment the optional memory device is a flash memory device. In an embodiment, the optional memory device may have up to 2 Giga bits of memory. The optional memory device allows the additional storage of data while the sensing device 100 is not streaming data to a host device over the wired and/or wireless communication networks. The additional storage is provided in order to ensure that there is no loss of data while the sensing device 100 is mobile, during communication network outages or while the power source 114 is interrupted while changing a battery. Furthermore, the data storage 106 may be used to store potentially month's worth of accelerometer data allowing for continuous operation and also providing a dual copy of data so that transmitted data may be checked.

The GPIO interface 126 provides an interface to I/O devices such as Light-emitting diodes (LEDs) 116. The LEDs 116 may be used as status indicators to indicate the current state of the sensing device 100.

In an embodiment support for wireless network communication is provided by a Bluetooth® and an IEEE 802.15.4 radio module. The Bluetooth® module is connected to the CPU directly via the USART 104 serial connection. The Bluetooth® link has a baud rate of 921.6 Kbps over the USART 104 and a free space transmission rate of 721 Kbps, with receiver sensitivity of −82 dBm.

The sensing device 100 is placed on top of an object that is associated with patient monitoring to detect when an action occurs that involves the object. There is no electrical connection and no communications path between the sensing device 100 and the object. The sensing device collects a time stamp associated with an action that is associated with the object that is being monitored and detected by the sensing device 100.

In an embodiment the object is a patient monitoring device. As there is no electrical connection and no communications path between the sensing device 100 and the patient monitoring device, the sensing device 100 may be used to detect physical actions related to the patient monitoring device irrespective of how the patient monitoring device may communicate the physical action.

The time stamp information received from a sensing device 100 by a collection device may be used to improve the accuracy of nurses' notes and to better interpret data with respect to time synchronization, motion detect and artifact reduction/false alarm suppression collected from various patient monitoring devices. Table 1 below illustrates an example of time stamp information that may be received from the sensing device.

TABLE 1

| |
|---|
| 39301.766977361774, 1.007, −0.526, 0.261, 1186511066.8440573 |
| 39301.766977598811, 0.687, −0.163, −0.044, 1186511066.8645372 |
| 39301.766977835847, 0.922, −0.243, −0.138, 1186511066.8850172 |
| 39301.766978072883, 0.463, −0.624, 0.734, 1186511066.9054971 |
| 39301.766978309919, 0.637, −0.546, 0.1052, 1186511066.925977 |

The table has five entries. Each entry represents a sample of data from a 3-axis accelerometer and the time the sample of data was stored. The entry includes five elements. The first element in the entry is a timestamp written in a Microsoft® Excel® compatible format representing the time that the sample of data was stored, for example, "39301.766977361774" in the first entry shown in Table 1. The next three elements are the values of the three axes of accelerometer data, for example, "1.007, −0.526, 0.261" in the first entry in Table 1. The fifth element is the timestamp in Universal Coordinated Time (UTC), for example, "1186511066.8440573" in the first entry in Table 1. The UTC timestamp format is typically used as an absolute measure for coordinating events and includes a date and time. The Excel™ compatible format is typically used by clinical nurses for data analysis.

In an embodiment a separate sensing device 100 may be placed on each of a plurality of patient monitoring devices in an Intensive Care Unit (ICU). Each respective one of the plurality of sensing devices may generate data (for example, a time stamp) indicating the time at which the sensed event occurred, for example, the time at which a push button on the patient monitoring device was touched or that the patient monitoring device was moved.

Figure 2:
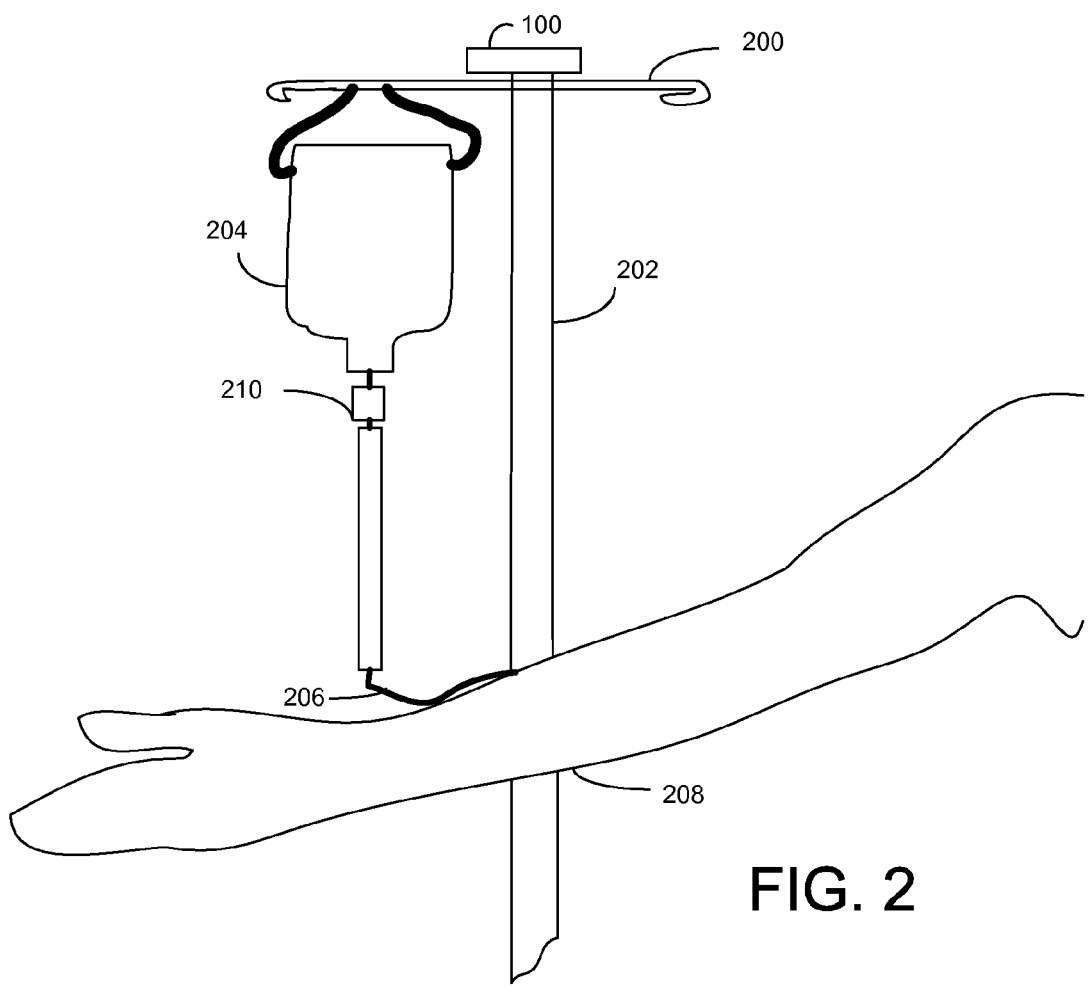
FIG. 2 illustrates an embodiment in which the sensing device monitors movement of a patient monitoring device.

FIG. 2 illustrates an embodiment in which the sensing device 100 monitors movement of a patient monitoring device. In the embodiment shown the patient monitoring device is an IV stand 200. The sensing device 100 is shown placed on top of an IV stand 200 to detect movement of the IV stand 200. The sensing device 100 may include an accelerometer acting as a switch that may be used to indicate that the IV stand 200 has been moved. For example, in an embodiment, an accelerometer may "act as a switch" using an on-device threshold measure. The sensing device 100 is "off" while the accelerometer values are below the threshold measure and the accelerometer is "on" while the accelerometer values are above the threshold measure. In an embodiment, the sensing device 100 may process the accelerometer data to extract features from the data such as the shareholding calculation used when the accelerometer is "acting as a switch". The processing of the accelerometer data (event data) may be performed by the CPU 102 in the microcontroller 101 and the processing of the event data may be used to detect the event when the accelerometer is acting as a switch.

The IV stand 200 provides support for an IV bag 204 that stores a fluid to be delivered to the patient. An IV line 206 is shown extending from the IV bag 204 and terminating in the arm 208 of a patient. An action by the caregiver may result in a movement in the IV stand 200, for example, when changing the flow rate through a flow rate button 210 and/or the IV bag 204 storing the fluid to be delivered through the IV line 206 to the patient. The movement of the IV stand 200 is detected by a motion sensor (accelerometer) in the sensing device 100. A raw signal from the accelerometer or data processed from the raw signal may be stored in the sensing device and/or transmitted to a collecting device indicating that the IV stand 200 has moved. The raw signal or processed data may be transmitted over a wired or wireless communications network to an event collecting system, for example, a remote host system.

The detection of the motion of the patient monitoring device with the accelerometer may be used to time-stamp clinical events. The time-stamp may be used to improve the timing in nurses' notes and to consolidate information about clinical events from multiple vendors' patient monitoring devices.

In another embodiment the patient monitoring device may be a blood pressure cuff. In this embodiment, the sensing device is placed on the blood pressure cuff and includes an accelerometer to detect motion. Upon detecting that the blood pressure cuff has been moved, a timestamp may be transmitted to the collection system. In one embodiment, the event data may be transmitted in binary format. In another embodiment, the event data may be expanded into a human readable form for display on a display device in the collection system prior to transmitting to the collection system. The recording of the date and time in the timestamp by the sensing device 100 prior to transmitting to the collection device ensures an accurate record of the time that the event was recorded. Furthermore, providing memory for storing the detected event and timestamp in the sensing device allows any errors in the original transmission over the wireless communication network to be corrected.

In an embodiment, using the handshaking between access points capability of the IEEE 802.15.4 wireless networks communication protocol, a sensing device on an IV pole may be tracked as it is moved from one access point to another, for example, anywhere in a hospital with sufficient access points.

Figure 3A:
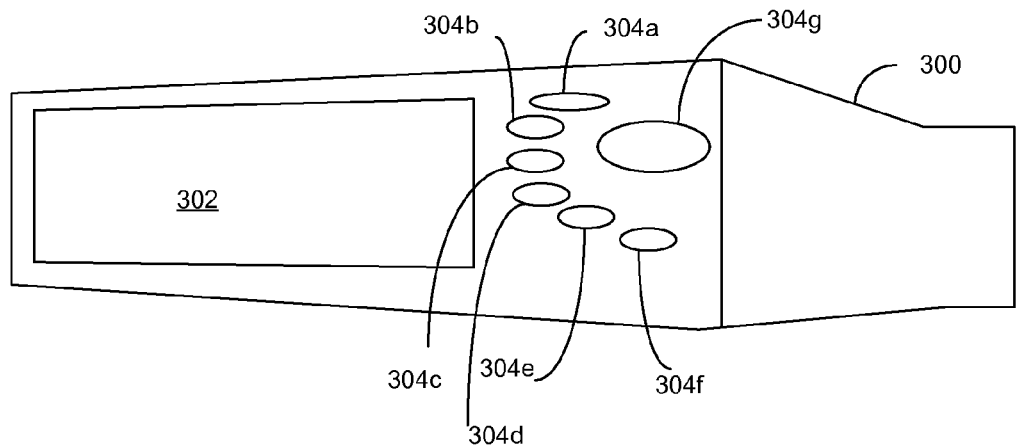
FIGS. 3A-3B illustrate an embodiment in which the sensing device monitors switches on a patient monitoring device.
Figure 3B:
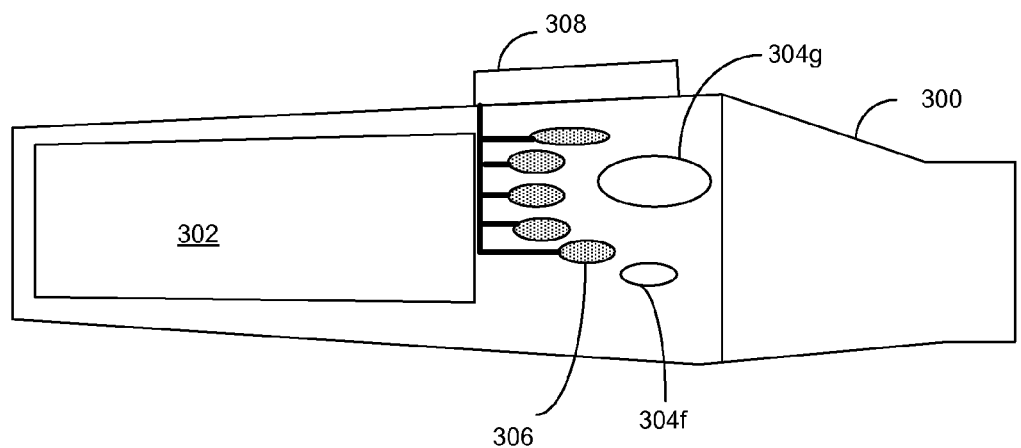

FIGS. 3A-3B illustrate an embodiment in which the sensing device 308 monitors switches on the patient monitoring device. Referring to FIG. 3A, the patient monitoring device 300 includes a display system that has a plurality of push buttons 304a-g. The display system includes a display 302 which is an electronic device such as a Cathode Ray Tube (CRT) or liquid crystal display (LCD)-based or gas plasma-based flat panel display that temporarily presents information in visual form. Each push button 304a-g is a small actuator that when pushed closes an electric circuit. The closing of the electric circuit denotes selection of a function that is mapped to the push button 304a-g.

FIG. 3B illustrates a sensing device 308 to monitor push buttons 304a-e on the patient monitoring device 300 shown in FIG. 3A. The sensing device 308 has at least one parasitic button press detector 306 that is placed on top of a push button 304a-g on the patient monitoring device 300 to detect a clinical event.

In this embodiment, parasitic switches 306 are placed over some or all of the push buttons 304 on the patient monitoring device 300. In an embodiment, a section of a flexible keyboard or keypad could be used to provide a parasitic switch. The flexible keyboard or keypad may include a Universal Serial Bus (USB) connection to allow communication between the sensing device and the flexible keyboard via a serial communications link. In another embodiment, the parasitic switches may be in the form of a flexible "membrane" keypad or an overlay keypad. In yet another embodiment, the parasitic switch may be a pressure sensitive switch that may be integrated into cloth.

Switch data generated by a parasitic switch placed over a regular switch on the patient monitoring device may be used to indicate that a button had been pressed (touched). In the embodiment shown in FIGS. 3A-3B, there are seven push buttons 304a-g and parasitic switches 306 have been placed over five of the push buttons 304a-e. The parasitic switches 306 are touch sensitive switches and are coupled to the sensing device 308. The sensing device 308 stores and/or broadcasts a time-stamped signal indicating when a push button 304a-e has been pressed as detected by the respective touch sensitive switch 306. Thus, there is no electrical connection and direct communications path between the patient monitoring device 300 and the sensing device 308. However, through the parasitic switches 306, the sensing device 308 detects the external force applied to a push button 304a-e on the patient monitoring device 300.

In an embodiment, a function in the patient monitoring device 300 may also be selected through the use of a virtual touch screen buttons displayed on a flat panel display 302. Each time a virtual touch screen button on the flat panel display is touched, information that includes a time-stamp indicating the date and time is transmitted to a collection device. A parasitic switch 306 may be placed over the virtual touch screen button on the flat panel display 302 to capture the touching of the virtual touch screen button. In one embodiment a "cancel" button in the sensing device 300 allows accidental activations to be negated.

Returning to FIG. 2, in another embodiment, the IV stand 200 may include a flow rate button 210 that may be a push button that may be used for changing the dose of medication to be delivered through the IV tube from the IV bag. The sensing device 101 may include a parasitic switch that is placed over a push button on the IV stand. In an embodiment, a touch-related event detected by the parasitic switch may indicate that the flow rate (dose) from the IV bag 204 has been manually changed, for example, increased/decreased, started or stopped.

In an embodiment, data from both the accelerometer and switches in the patient monitoring device may be used to automatically create annotations specifying the time at which the action (event) (motion-oriented and/or button pressing) was detected.

Figure 4:
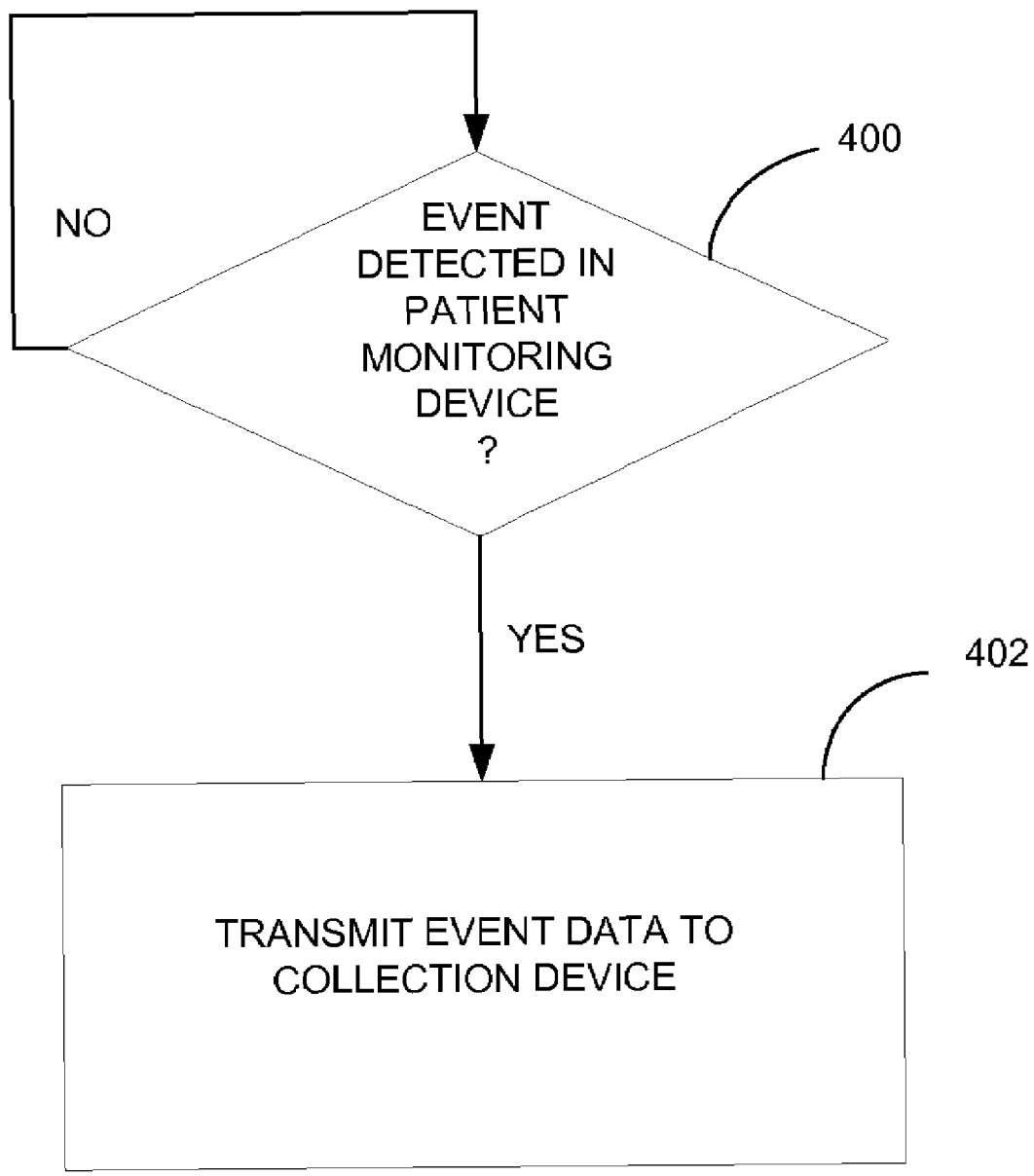
FIG. 4 is a flowgraph illustrating a method for monitoring an event in a patient monitoring device.

FIG. 4 is a flowgraph illustrating a method for monitoring an event in a patient monitoring device.

At block 400, the sensing device 100 which has been placed on the patient monitoring device continuously monitors sensors to detect movement of the patient monitoring device and/or that a button on the patient monitoring device has been touched. If an event is detected, processing continues with block 402. If not, processing continues with block 400.

At block 402, an event has been detected, the raw data associated with the event is stored in memory in the sensing device for transmitting later to a collection system and/or is transmitted to a collection system. The data transmitted to the collection system may be used by a caregiver to provide the time of events that may be recorded in the patient's medical record. Processing continues with block 400, to monitor the patient monitoring device for a next event.

The sensing device provides an automatic way to improve the timing of events related to patient monitoring in medical records (caregivers' notes) and improves accuracy of medical records used for making clinical decisions such as the time that medications were actually administered. The sensing device may also provide a method to automatically time synchronize to help consolidate clinical data from patient monitoring devices manufactured by different vendors. As the sensing device may provide caregivers with more complete/correct information this may improve clinical outcomes for patients.

It will be apparent to those of ordinary skill in the art that methods involved in embodiments of the present invention may be embodied in a computer program product that includes a computer usable medium. For example, such a computer usable medium may consist of a read only memory device, such as a Compact Disk Read Only Memory (CD ROM) disk or conventional ROM devices, or a computer diskette, having a computer readable program code stored thereon.

While embodiments of the invention have been particularly shown and described with references to embodiments thereof, it will be understood by those skilled in the art that various changes in form and details may be made therein without departing from the scope of embodiments of the invention encompassed by the appended claims.

The invention claimed is:

1. An apparatus comprising:
   a sensor to detect an event due to an action associated with a force applied to a patient monitoring device by a caregiver, the sensor having no communications path and no electrical connection to the patient monitoring device;
   an event timer to record a time at which the detected event occurs; and
   a wireless communication network interface to transmit the detected event and the recorded time to a collection system.

2. The apparatus of claim 1, wherein the patient monitoring device is an IV stand.

3. The apparatus of claim 1, wherein the sensor is an accelerometer to detect motion of the patient monitoring device.

4. The apparatus of claim 1, wherein the sensor is a parasitic switch that is placed over a push button in the patient monitoring device to detect an external force applied to the push button by the caregiver.

5. The apparatus of claim 1, wherein the patient monitoring device is an electrocardiogram monitor.

6. The apparatus of claim 5, wherein the sensor is a parasitic switch that is placed over a push button in the electrocardiogram monitor to detect an external force applied to the push button by the caregiver.

7. The apparatus of claim 1, further comprising:
   memory to store the event and associated timestamp prior to transmitting to the collection device.

8. The apparatus of claim 1, further comprising:
   a processor to process event data received from the sensor to detect the event.

9. A method comprising:
   detecting, by a sensor, an action associated with a force applied to a patient monitoring device by a caregiver, the sensor having no communications path and no electrical connection to the patient monitoring device;
   recording a time at which the detected event occurred; and
   transmitting the detected event and the recorded time to a collection system via a wireless communication network interface.

10. The method of claim 9, wherein the patient monitoring device is an IV stand.

11. The method of claim 9, wherein the sensor is an accelerometer to detect motion of the patient monitoring device.

12. The method of claim 9, wherein the sensor is a parasitic switch that is placed over a push button in the patient monitoring device to detect the force applied to the push button by the caregiver.

13. The method of claim 9, wherein the patient monitoring device is an electrocardiogram monitor.

14. The method of claim 13, wherein the sensor is a parasitic switch that is placed over a push button in the electrocardiogram monitor to detect the force applied to the push button by the caregiver.

15. The method of claim 9, further comprising:
    storing the event and associated timestamp prior to transmitting to the collection device.

16. The method of claim 9, further comprising:
    processing event data received from the sensor to detect the event.

17. The method of claim 9, wherein the sensor is placed on and is in physical contact with the patient monitoring device.

18. The method of claim 9, wherein the detected event and recorded time is transmitted to the collection system for use in conjunction with other information to corroborate an action performed by the caregiver.

19. The apparatus of claim 1, wherein the sensor is placed on and is in physical contact with the patient monitoring device.

20. The apparatus of claim 9, wherein the detected event and recorded time is transmitted to the collection system for use in conjunction with other information to corroborate an action performed by the caregiver.

* * * * *